US00PP11401P

United States Patent [19]

Kent

[11] Patent Number: Plant 11,401

[45] Date of Patent: Jun. 6, 2000

[54] BROMELIAD PLANT NAMED 'GUZ 216'

[75] Inventor: Jeffrey C. Kent, Vista, Calif.

[73] Assignee: Kent's Bromeliad Nursery, Inc., Vista, Calif.

[21] Appl. No.: 09/115,194

[22] Filed: Jul. 13, 1998

[51] Int. Cl.[7] ..... A01H 5/00

[52] U.S. Cl. ..... Plt./371

[58] Field of Search ..... Plt./371

[56] References Cited

U.S. PATENT DOCUMENTS

P.P. 10,383 5/1998 Bos ..... Plt./371

*Primary Examiner*—Lynette R. F. Smith
*Assistant Examiner*—Wendy A Baker
*Attorney, Agent, or Firm*—James A. Lucas; Driggs, Lucas, Brubaker & Hogg Co., L.P.A.

[57] ABSTRACT

A medium sized Guzmania hybrid that has a uniform variegation throughout and a suffusion of red color blending into the yellow color of the floral bracts after anthesis. The variegation brightens the colors of the parent.

1 Drawing Sheet

BACKGROUND OF THE INVENTION

The present invention relates to a new and distinct variety of plant in the genus Guzmania within the Bromeliad plant family. This application relates to a newly developed interspecific hybrid Guzmania plant resulting from a planned breeding program which I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Included objects of my program are to produce plants which will be attractive to the consumer; which will develop reasonably rapidly under controlled conditions; and, retain for a long term, highly attractive and bright inflorescence; i.e., bract coloration, after being induced into the flowering stage. It is a specific object to provide a low maintenance plant which will be long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by division while continuing the distinctive characteristics of the plants through progressive clonal generations.

SUMMARY OF THE INVENTION

The plant was a naturally occuring, vegetative sport discovered as a single plant growing in a cultivated planting of *Guzmania* 'Remembrance' (unpatented in the U.S.). 'Remembrance' is a hybrid of the seed parent *Guzmania zahnii* 'Panama' (unpatented) and the pollen parent *Guzmania lingulata* 'Costa Rica' (unpatented). With the recognition that this sport satisfied the objects of the breeding program, it was isloated and set aside for further observation and testing. The resulting selection has been assigned the designation 'GUZ 216' for purposes of identification. This plant has been reproduced by division at Vista, Calif. and elsewhere, and the clonal specimens resulting have been determined to be identical to the original selection in all distinguishing characteristics. The superior attributes of this plant will be revealed in the botanical description to follow.

The characteristics of the plant 'GUZ 216' may be summarized as follows:

The leaves are medium size and linear, smooth and acuminate in shape. They are medium olive green in color and are variegated with ¼" yellow-white bars and occasional thin lines toward their center. The margins of the leaf bases are stained scarlet red in color toward the base merging to all scarlet red to the base of the inflorescence. Some of the variegation on the basal leaves is also scarlet red.

The characteristics of the floral bracts and scape bracts are also unusual inasmuch as the scarlet red coloration of the floral bract blend into a bright canary yellow of the upper portion of the scape bracts.

The combination of the variegation which is uniform throughout the plant in conjunction with the suffusion of the scarlet red bract coloration blending with the canary yellow of the floral bract after anthesis provide a lighter and brighter presence than that of the parent 'Remembrance'. This overall impression is due to the combination of colors which collectively appear to illuminate the appearance of the individual colors which are in the combination.

BRIEF DESCRIPTION OF THE VIEW OF THE DRAWING

The single color photograph of the drawing depicts a mature specimen of the plant in top perspective angle in mid to late flowering stage. Illustrated are the mature leaves and the spike. The relative sizes of the lower, splayed intermediate and terminal bracts can be seen by the angle of the illustration.

The time period from liner to market stage is approximately two years. The plant has a prolific propensity to develop side-shoots with the general number of leaves and bracts being about 16 when produced for optimum market stage.

The color definitions in the specification to follow have been taken from the R.H.S. Colour Chart of The Royal Horicultural Society. While colors depicted are believed to be of a high level of color fidelity, the coloration of this plant should be understood to be approximate, and somewhat variable as a function of cultural conditions and horticultural practices. For example, the bract color might slightly fade if the plant is cultured in bright light; the leaf color can be varied by the composition and concentration of fertilizer applied to specimens of the plant.

BOTANICAL DESCRIPTION OF THE PLANT

Parentage: Sport of Guzmania 'Remembrance'.

Propagation:

*Method of asexual reproduction.*—Division.

*Where reproduction took place.*—Kent's Bromeliad Nursery 1266 Ridge Rd., Vista, Calif. 92083.

Plant: Monocot Perennial. Medium in size Overall height from soil surface including inflorescence 15" to 17". Overall width–21" to 22". Vigorous in growth to anthesis relative to other variegated bromeliads Spreading and drooping Dense Vase formed Hardiness at temperatures below 32° F. Tender This variety has comparable resistance to plant disease as other Guzmania cultivars.

Leaves:

*Length.*—14" to 16".

*Width.*—1¼" at base. Medium in size. Linear. Acuminate. Acutely pointed. Medium thickness. Medium green in color. Smooth: Leaves 146-A in color, obverse and reverse Variegated with ¼" bars longitudinally, with occasional thin lines toward the center, both 2-D in color. Margins of leaf bases stained 45-C in color toward the base, merging to all 45-C upwards to the base of the inflorescence, obverse and reverse. Some of the striping on the leaves 45-C in color on the basal leaves, mainly on the reverse.

*Inflorescence.*—Branched spike.

Flower buds: Tender. Medium in size (1¼"×¼") in size just before opening. Long in length compared to those of other bromeliads. Pointed and appressed.

*Color.*—155-D.

*Scape bracts.*—Linear acute to deltoid 4"×1¼" at base of inflorescence decreasing to 2½"×¼" at apex. 45-C in color, obverse and reverse, color decreasing down the stem, staining the bracts at the base of the inflorescence 1⅛"×½" 6-B in color fading to 7-A post anthesis. Observed length—10" to 12".

*Floral bracts.*—Deltoid in shape 1⅛"×½" 45-C in color on lower bracts, gradually suffused with 6-C color upwards increasing to all 6-C in color, replacing 45-C at apex of inflorescence.

Flowers:

*Corolla.*—Cylindrical, acute 6-C in color. 3 sepals ⅞"×1⅛", 8-C in color fading to 8-D at base, blackening with age. 3 petals 1½"×3/16" scarcely open at anthesis, 6-C in color, joined the lower 1¼".

Fruit: A three-celled capsule splitting longitudinally when mature; seeds with pappus.

What is claimed is:

1. A new and distinct variety of Guzmania plant substantially shown and described characterized by uniform variegation throughout the plant, a suffusion of red color blending in with the yellow color of the floral bracts after anthesis, said floral bracts remaining in color for a period of between three and four months.

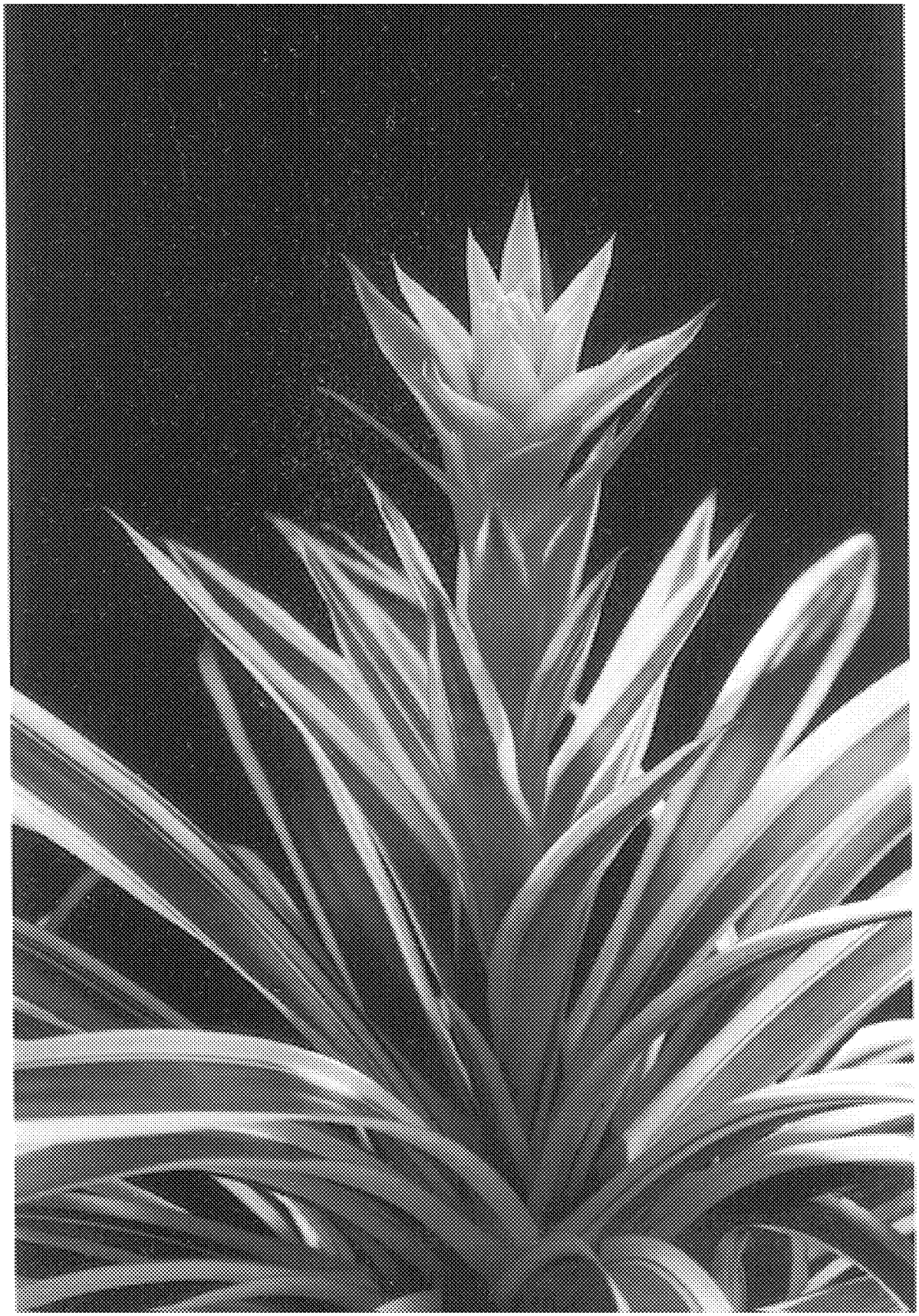

* * * * *